(12) United States Patent
Beitzel et al.

(10) Patent No.: US 8,911,756 B2
(45) Date of Patent: Dec. 16, 2014

(54) WINDOW STICKER FOR ATTRACTING AND DESTROYING INSECTS

(75) Inventors: Else Beitzel, Andernach (DE); Hermann-Josef Jaeckels, Bendorf (DE); Malgorzata Kloczko, Neustadt/Wied (DE); Birgit Kocherscheidt, Bonefeld (DE); Thomas Böcker, Leichlingen (DE)

(73) Assignee: ICS Innovative Care Systems, Andernach (DE)

( * ) Notice: Subject to any disclaimer, the term of this patent is extended or adjusted under 35 U.S.C. 154(b) by 812 days.

(21) Appl. No.: 12/641,402

(22) Filed: Dec. 18, 2009

(65) Prior Publication Data

US 2010/0158965 A1 Jun. 24, 2010

(30) Foreign Application Priority Data

Dec. 19, 2008 (DE) .......................... 10 2008 063 807

(51) Int. Cl.
*A01N 25/00* (2006.01)
*A01N 25/34* (2006.01)
(52) U.S. Cl.
CPC ..................................... *A01N 25/34* (2013.01)
USPC .......................................................... 424/405
(58) Field of Classification Search
CPC ........ A01N 25/34; A01N 25/24; A01N 25/10
See application file for complete search history.

(56) References Cited

U.S. PATENT DOCUMENTS

| 2,911,756 | A | * | 11/1959 | Geary ............................. | 43/114 |
| 4,047,505 | A | * | 9/1977 | McAndless .................... | 119/654 |
| 2007/0148202 | A1 | * | 6/2007 | Primo Yufera et al. ........ | 424/410 |
| 2008/0050433 | A1 | * | 2/2008 | Roreger et al. ............... | 424/484 |

FOREIGN PATENT DOCUMENTS

| DE | 690 09 769 | | 6/1994 | |
| DE | 10 2006 058 252 | | 6/2008 | |
| DE | 102006058252 | * | 12/2008 | ............. A01M 1/20 |
| EP | 0 446 464 | | 9/1991 | |
| EP | 1 191 054 | | 3/2007 | |

OTHER PUBLICATIONS

"Primojel® and Primellose® Superdisintegrants" product over-view brochure. DMV Fonterra Excipients. pp. 1-6, Aug. 2008.

* cited by examiner

*Primary Examiner* — Lezah Roberts
*Assistant Examiner* — Nannette Holloman
(74) *Attorney, Agent, or Firm* — Frommer Lawrence & Haug LLP

(57) ABSTRACT

There is disclosed a product for attracting and destroying insects which comprises an active-substance-comprising bait layer (1) together with a bait substance and an insecticide. The active-substance-comprising bait layer (1) furthermore comprises a superdisintegrant whose effect is that, upon the use of the product in an environment with high atmospheric humidity, the active-substance-comprising bait layer (1) does not run.

22 Claims, 2 Drawing Sheets

WINDOW STICKER FOR ATTRACTING AND DESTROYING INSECTS

It has emerged that when using the known product in an environment with a high relative atmospheric humidity, running of the active-substance-comprising layer is observed. This manifests itself in the fact that water droplets form in the layer which comprises the combination of feed substance and/or bait attractant and insecticide and which initially appears outwardly homogeneous, and these water droplets increase in size in the course of time. Due to the vertical arrangement on a windowpane, the water droplets first coalesce and finally spread, which, ultimately, also leads to wetting of the windowpane.

This running or spreading is a defect on coatings known from the field of coating technology, and it occurs while the coating layer during the processing on vertical faces of the object to be coated is still in the liquid state. The fairly obvious coating defect of the phenomenon referred to in the technical language as "sagging" leads to "curtaining" and "runs". In extreme cases, said layer, which comprises the combination of feed substance and/or bait attractant and an insecticidal active substance may dissolve completely, rendering the product ineffective.

A further disadvantage of the known fly window stickers was observed when exhausted products were peeled off from a windowpane. In some cases, the layer which comprises the combination of feed substance and/or bait attractant and insecticide became detached from the further constituents of the window fly sticker. In addition, it was also observed that this layer itself disintegrated to form smaller parts. Such a crumbling of the layer comprising the combination of feed substance and bait attractant required a separate disposal step in the form of sweeping up or hoovering up.

It is an object of the present invention to provide a window fly sticker for attracting and destroying insects, where the danger of dissolving the layer which comprises the feed substance or bait attractant is reduced or even avoided, in particular upon the action of water in the liquid or gaseous state.

Furthermore, it is intended to solve the problem of the insufficient adherence of this layer on the further components of the window fly sticker, in particular a backing layer.

Finally, an object of the present invention is also the improvement of the cohesion of a layer which comprises a feed substance and/or bait attractant.

The object is achieved by a product for attracting and destroying insects, which product comprises at least one active-substance-comprising bait layer (1) and a backing film (2). In the active-substance-comprising bait layer (1), the product comprises a superdisintegrant, besides a bait substance. As the agent for destroying insects, the product comprises at least one insecticide.

In a particular embodiment, the product has an anchoring layer (4), which is arranged between the active-substance-comprising bait layer (1) and the backing film (2).

In a further embodiment, the product may additionally have an adhesive layer (3).

To cover the adhesive layer (3), the product may, before its use, be equipped with a protective paper (6). The active-substance-comprising bait layer (1) may also be equipped until its use with a protective paper (5).

Finally, the product may also have decorative elements which exert or enhance an attractant effect on insects.

In an advantageous embodiment, the product is designed as a window sticker. Further advantageous embodiments are erectable traps and tags.

The object is furthermore solved by a method of preparing a product for attracting and destroying insects, which has at least one active-substance-comprising bait layer (1) and a backing film (2), where, in a first step, at least one bait substance and at least one insecticide are mixed. In this step, it is also possible to add at least one adjuvant which acts as solvent for the insecticide and/or the bait substance, at least one auxiliary, at least one attractant and/or at least one bittering agent to the mixture. If appropriate, this first step may be carried out with heating and/or with the addition of water.

In a second step, the superdisintegrant is added to the mixture obtained in the first step.

The resulting mixture is subsequently applied to the backing film (2) by means of a suitable application step. Suitable methods may be printing methods, such as flexographic printing, screen printing, pad printing and the like, but also methods such as coating, extruding, knife-coating, spraying and the like. A preferred application method is rotary screen printing.

After the mixture obtained in the second step has been applied to the backing film (2), a laminate of an active-substance-comprising bait layer (1) and a backing film (2) is formed. Any solvent(s) present—in particular water—is/are removed, preferably by drying and at elevated temperature (between 30° C. and 90° C., preferably between 45° C. and 85° C.). Here, the water content should, naturally, be as low as possible, at least less than 5% by weight, preferably less than 2% by weight.

The active-substance-comprising bait layer (1) of this laminate can now be covered with a protective paper (5).

The bi- or multilayer laminate of at least one active-substance-comprising bait layer (1) and at least one backing film (2) can be cut into strips with suitable predetermined dimensions by means of longitudinal and transverse cutting.

In another embodiment of the method, it is also possible to punch circular punchings with a predetermined diameter from said laminate; however, any other shapes such as oval or shapes which correspond to the printed-on motifs (flowers etc.) are also possible.

In these cases, residual superfluous punch material is preferably peeled off and discarded. It is also possible to introduce holes into the laminate of at least one active-substance-comprising bait layer (1) and at least one backing film (2), which holes can later serve for hanging. A hook shape on the outside of the laminate may also act as attachment device.

The bi- or multilayer laminate of at least one active-substance-comprising bait layer (1) and at least one backing film (2) can also be additionally equipped with perforations and/or folding lines. The product can then be folded by the user along these perforations or fold lines so that, in this manner, a three-dimensional hollow article is formed. Such folds can therefore make possible secure erecting of the product, whereby the user has available an erectable trap.

Bi- or multilayer products are obtained and these products can be packaged in side-sealed bags, tubular bags, flat bags, covering paper, covering film, thermoformed blisters and/or cardboard boxes.

In a preferred embodiment of the preparation method, a backing film (2) is used where an anchoring layer (4) has been applied to one side before applying the mixture obtained in the second step. The mixture obtained in the second step is then applied to this anchoring layer (4).

In a further embodiment, an adhesive layer (3) can additionally be applied to that side of the backing film (2) which faces away from the mixture to be applied. This is preferably done before applying the mixture by coating and preferably by subsequently laminating on a protective paper (6).

The decorative elements of the product are likewise preferably applied to the backing film (2) before applying the mixture, preferably by printing processes.

Finally, a further solution according to the invention is the use of the product which has at least one active-substance-comprising bait layer (1) and a backing film (2) for attracting and destroying insects.

A further solution is an anchoring layer (4) for improving the adherence of different materials—in particular the components of the active-substance-comprising bait layer (1)—to a backing film.

Finally, a further subject matter of the present invention is the use of a superdisintegrant for producing a layer with improved cohesion and which comprises a bait substance, in particular sugar.

The active-substance-comprising bait layer (1) is understood as meaning that component of the product which comprises at least one bait substance and at least one insecticide.

The active-substance-comprising bait layer (1) has an areal weight in the range of between 10 and 250 g/m$^2$, preferably in the range of between 20 and 50 g/m$^2$. The area of the active-substance-comprising bait layer (1) for a single product is between 10 and 300 cm$^2$, preferably between 50 and 150 cm$^2$.

The active-substance-comprising bait layer (1) forms the top layer of the product. This ensures that, when the product is used, an insect can easily come into contact with the active-substance-comprising bait layer. The insecticide is taken up simultaneously with the bait substance.

The insecticide is present in the active-substance-comprising bait layer (1) at a concentration of between 0.1 and 25% by weight, preferably at a concentration of between 0.5 and 10% by weight.

During storage of the product, the active-substance-comprising bait layer can be covered with a protective paper (5) which is peeled away from the active-substance-comprising bait layer shortly before using the product.

The active-substance-comprising bait layer (1) can be present in the form of a continuous layer, preferably with an approximately constant thickness.

The active-substance-comprising bait layer (1), however, may also be present in the form of a noncontinuous layer. In this discontinuous case, the active-substance-comprising bait layer can be present for example in the form of dots and/or strips which are not fully in contact with one another. Such shapes of the active-substance-comprising bait layer (1) can be obtained by adapting the application methods in question. Here, suitable stencils may be placed on the backing film in order to protect areas on the backing film against application of the mixture of at least one bait substance, at least one insecticide and the superdisintegrant.

The area of the active-substance-comprising bait layer may, in specific embodiments, be smaller than the area of the backing film (2), which is readily achieved by not coating the entire area of the backing film (2).

The active-substance-comprising bait layer (1) may also be present as a solid foam, in particular as a rigid foam, a semi-rigid foam or a soft foam. In a particular embodiment, it takes the form of an elastic foam. Especially preferred is the embodiment of the active-substance-comprising bait layer (1) as a soft foam which upon application of pressure (compressive strength at 10% deflection as specified in DIN 53421) has a dimensional stability of 15 kPa or less. Basic polymers such as formaldehyde resins, polyisocyanurates (PIRs), polystyrene, polyurethanes (PURs) and polyvinyl chloride are used for preparing an active-substance-comprising bait layer (1) in the form of a rigid foam.

In principle, the insecticide on the one hand and the bait substance together with the superdisintegrant on the other hand may also be present, in the product, in two separate, preferably adjacent, layers. However, such an embodiment requires two separate starting materials to be provided which must be applied to the backing film (2) in two separate process steps. Such an embodiment is not preferred on the basis of economic considerations, even if it does not result in technical problems in principle.

The product comprises a backing film (2) which is arranged underneath the at least one active-substance-comprising bait layer (1). The backing film (2) may take the form of paper, board or metal film, but it is preferably a—preferably transparent—film made of a polymeric material. Suitable are single or laminate films with a thickness of between 5 and 150 μm, preferably between 25 and 75 μm.

The backing film (2) has the function of imparting handling ability to the product and of making possible the application of flowable components during the preparation process. The area of the backing film (2) is preferably identical to the area of the active-substance-comprising bait layer (1).

In a particular embodiment, however, the area of the backing film (2) can also be greater than the area of the active-substance-comprising bait layer (1) and/or the adhesive layer (3) in order to provide a gripping aid for the simple peeling of an exhausted product (in particular in the form of a window sticker) away from the site of application.

Materials which are suitable for the backing film (2) are polyethylene (PE), polyethylene terephthalate (PET), polyvinyl chloride (PVC), polyester, polypropylene (PP), cellophane, cellulose, polyvinylidene chloride, polystyrene, board, board laminate, PET/board/PET laminate and other raw materials. Preferred are polyethylene (PE), polypropylene and polyethylene terephthalate (PET).

The product may comprise an adhesive layer (3) which brings about adherence to a solid surface. The adhesive layer therefore preferably comprises a pressure-sensitive adhesive. By having "pressure-sensitive adhesive properties" there is understood the fact that, after gentle pressing-on, the adhesive layer in the dry state and at room temperature adheres to a multiplicity of surfaces from which, when required, it can again be peeled off without leaving residues.

Pressure-sensitive adhesives are known to the skilled worker. They include synthetic and natural rubber, butyl rubber, styrene/butadiene copolymers, ethylene/vinyl acetate copolymers, acrylonitrile copolymers, polychloroprene, polyisobutylene, polyvinylethers, SBS block polymers, SIS block polymers, polyacrylates, polyesters, polyurethanes and polysiloxanes. To achieve the required pressure-sensitive adhesive properties, these basic materials can additionally be admixed with materials such as resins, plasticizers, fillers and stabilizers.

Especially preferred as pressure-sensitive adhesives for the adhesive layer are polyacrylates, polyisobutylenes and ethylene/vinyl acetate copolymers.

The preferred pressure-sensitive adhesives have a glass transition temperature in the range of from −20° C. to −70° C.

The adhesive layer (3) has a layer thickness in the range of between 10 μm and 150 μm, preferably in the range of between 20 μm and 70 μm.

The area of the pressure-sensitive adhesive layer preferably corresponds to the area which is also covered by the active-substance-comprising bait layer (1) or the backing film (2). However, the area may also be substantially smaller and be designed for example in the form of a narrow strip or of individual dots.

The adhesive layer forms the bottom-most layer of the product when used. During storage, this adhesive layer is preferably covered by a protective paper (6) which is peeled away from this layer shortly before using the product.

The peel resistance of the adhesive layer for a 180° peel is preferably in the range of less than 10 N/25 mm, especially preferably in the range between 1 and 6 N (as specified in DIN EN 1464).

Suitable solid surfaces are, in particular, windowpanes (made of glass or plastic), but also tiles, tiled walls, furniture (made of plastic or wood), window frames, wallpaper and the like. As an erectable trap, the product can be placed on any support, in particular in closed spaces.

Suitable as bait substance are mainly sugars. These include: monosaccharides, disaccharides and mixtures comprising mono- and/or disaccharides. Sugar alcohols (alditols) are also among the suitable bait substances, in particular xylitol, D-glucitol ("sorbitol"), D-mannitol, maltitol, isomalt and lactitol.

Suitable monosaccharides are L-arabinose, D-xylose, D-ribulose, D-glucose ("grape sugar"), D-mannose, D-galactose, D-glucuronic acid (also as glucuronate or esterified), D-galacturonic acid (also as galacturonate or esterified), N-acetyl-D-glucosamine, D-glucosamine, N-acetyl-D-galactosamine, D-fucose, L-fucose, L-rhamnose, D-chinovose and D-fructose ("fruit sugar").

Preferred monosaccharides are D-glucose and D-fructose. Suitable disaccharides are maltose ("malt sugar"), cellobiose, isomaltose, isomaltulose, gentiobiose, trehalose, sucrose ("cane sugar" or "beet sugar"), lactose ("milk sugar") and laminaribiose.

Preferred disaccharides are lactose, maltose and sucrose.

The preferred sugar alcohol is D-glucitol.

The suitable mixtures which comprise mono- and/or disaccharides include maple sap, maple syrup, baker's honey, blossom honey, glucose syrup, honey, honeydew honey, industrial honey, invert sugar, invert syrup, isoglucose, isomerate sugar, maize syrup, maltose syrup, treacle, corn syrup and molasses.

The suitable mixtures also include honey and also forest honey (which the bees do not produce from nectar, but from honeydew, suitable plants being broad-leaf and coniferous trees which grow in forests, such as sycamore (*Acer pseudoplatanus*), field maple (*Acer campestre*), Norway maple (*Acer platanoides*), sessile oak (*Quercus petraea*), English oak (*Quercus robur*), Norway spruce (*Picea abies*), Scots pine (*Pinus sylvestris*), larch (*Latrix decidua*) and silver fir (*Abies alba*)).

Preferred mixtures are glucose syrup and maltose syrup.

The concentration of the bait substance in the active-substance-comprising bait layer (1) should be as high as possible in order to maximize the attractant effect of the product. The concentration of the bait substance can therefore amount to up to 99.5% by weight, it is preferably between 50 and 95% by weight, especially preferably between 70 and 90% by weight. A concentration of 30% by weight of bait substance in the active-substance-comprising bait layer (1) can be considered to be an expedient lower limit.

Suitable insecticides are natural and synthetic insecticides. The natural insecticides include pyrethrum, an extract from dried chrysanthemum flowers which comprises pyrethrins, cinerins and jasmolins. The synthetic insecticides include in particular organic insecticides from the following classes of compounds: organophosphorus insecticides (for example parathion, dimethoate), carbamates (for example carbaryl, carbofuran, propoxur), pyrethroides (for example allethrin, cyfluthrin, permethrin), phenylpyrazoles (for example fipronil) and neonicotinoides (for example acetamiprid, imidacloprid, clothianidin, thiacloprid and thiametoxam).

Since the use of these substances in the domestic field and in private gardens requires official approval, only those insecticides which also meet the approval requirements (i.e. the legal provisions in these fields: the Pflanzenschutzmittelgesetz [Plant Protectant Act], the Chemikaliengesetz [Chemicals Act], the Biozidgesetz [Biocide Act] and the like) are suitable. The insecticides employed here mainly act via the nervous system or the respiratory chain.

Preferred insecticides are those which bring about rapid destruction of the insect.

Specifically, the following natural or synthetic insecticides may be mentioned as being suitable: abamectin, acetamiprid, alpha-cypermethrin, azadirachtin (neem), azamethiphos, beta-cyfluthrin, bifenazate, bifenthrin, buprofezin, chlorantraniliprole, chlorfenapyr, chlorpyrifos, clothianidin, deltamethrin, diflubenzuron, dinotefuran, dimethoate, esfenvalerate, etofenprox, fenoxycarb, fenpyroximate, flonicamid, flubendiamid, flufenoxuron, imidacloprid, imiprothrin, indoxacarb, potash soap, kieselguhr, lambda-cyhalothrin, lithium perfluoroctanesulphonate, magnesium phosphide, metaflumizone, methoxyfenozide, metofluthrin, milbemectin, mineral oils, n-methylneodecanamide, nicarbazin, novaluron, pirimicarb, pirimiphos-methyl, pymetrozine, pyrethrins, pyridalyl, rapeseed oil, spinosad, spirodiclofen, sulphuryl fluoride, tebufenozide, tefluthrin, thiacloprid, thiamethoxam and zeta-cypermethrin.

Also suitable are biopesticides such as *Bacillus thuringiensis* subspecies and Mexican *Cydia pomonella* granulovirus.

Combinations of at least two insecticides are also suitable, such as, for example, abamectin thiamethoxam, azamethiphos+fipronil, beta-cyfluthrin clothianidin, beta-cyfluthrin imidacloprid, cyfluthrin+codlemone, fludioxonil+metalaxyl-M+thiamethoxam, fuberidazole+imazalil+triadimenol+imidacloprid, methiocarb+imidacloprid, pencycuron+imidacloprid, pyrethrins+abamectin, pyrethrins rapeseed oil and tefluthrin+imidacloprid.

Especially preferred as insecticide are acetamiprid, azamethiphos, ethofenprox, fipronil, imidacloprid, the pyrethroids and thiacloprid, and the combination of azamethiphos and fipronil.

The active-substance-comprising bait layer (1) can also comprise at least one adjuvant which acts as solvent for the insecticide and/or the bait substance. Suitable solvents are, inter alia, aliphatic hydrocarbons, aromatic hydrocarbons, hydroaromatic hydrocarbons, terpene hydrocarbons, alcohols, esters, ethers, glycol ethers, ketones, chlorohydrocarbons, aldehydes, acetals and aliphatic saturated monocarboxylic acids.

EXAMPLEs which may be mentioned are: 1-octanol, 1-decanol, acetone, acetophenone, benzyl alcohol, butyrolactone, hexyl laurate, PEG-60 corn glycerides with the trade name Crovol M 70, citrus terpenes, dimethylformamide, dimethyl sulphoxide, acetic acid, ethanol, ethyl acetate, ethylene glycol, eucalyptol, glycerol, isopropyl myristate, methyl ethyl ketone, morpholine, lavender/citronella mixture, myrcene, neodecanoic acid, N-methyl-2-pyrrolidone (NMP), N-octylpyrrolidone (NOP), oleic acid, PEG 400, PLURONIC PE 4300, Proglyde DMM, dilute hydrochloric acid, tributyl phosphate, Triton X-100 and water. Especially preferred are methylpyrrolidone (NMP), N-octylpyrrolidone (NOP) and butyrolactone.

Suitable solvents for the insecticide may also be natural or synthetic polymers.

The active-substance-comprising bait layer (1) can also comprise at least one of the following auxiliaries: binders, UV absorbents, pH buffers, salts, antiageing agents (antioxidants and antiozonants), fillers, plasticizers, odour-masking agents, deoxidizers, antistatics, stabilizers, separating agents, glidants, flame retardants, microbicides, viscosity enhancers, detergents, dispersants, optical brighteners, colorants and flavourings.

The active-substance-comprising bait layer (1) can also comprise at least one attractant from the group of the insect pheromones. These include the sexual pheromones and aggregation pheromones produced by the insects themselves, such as anastrephin, bombycol, brevicomin, chalcogran, cucujolide, disparlure, dominicalure, epoxypolyene, ferrulactone, frontalin, grandisol, hepialon, ipsdienol, lardolure, lineatin, matsuon, muscalure, multistriatin, olean, periplanone, pityol, quadrilure, rhynchophorol, serricornin, stegobinon, sulcatol, verbenol and others. If present in the active-substance-comprising bait layer (1), such insect pheromones are present at a concentration of from 0.01 to 0.2% by weight, preferably from 0.05 to 0.1% by weight.

In an especially preferred embodiment, the active-substance-comprising bait layer (1) comprises at least one bittering agent which is intended to keep pets and/or toddlers from unintentionally consuming it.

It has emerged that the use of a superdisintegrant reduces or indeed eliminates the risk of dissolution of the constituent which comprises the bait substance. To this end, the superdisintegrant may be present in a separate layer adjacent to the active-substance-comprising bait layer (1). Preferably, however, the superdisintegrant is present in the active-substance-comprising bait layer (1) to ensure more thorough mixing of bait substance and superdisintegrant.

Superdisintegrants which are suitable are substances which are employed in tableting technology as disintegration aids. They are adjuvants which ensure that tablets rapidly disintegrate in water or gastric juice and that the pharmaceuticals are released in absorbable form. In this context, suitable substances are those with a high water absorption capacity, for example starch, cellulose derivatives, alginates, dextrans, crosslinked polyvinylpyrrolidone and others.

The fact that the use of such a superdisintegrant ensures the physical stability and integrity of the active-substance-comprising bait layer (1) over a prolonged period despite the action of moisture is all the more astonishing since these substances have been used precisely for the rapid disintegration of tablets.

If present in the active-substance-comprising bait layer (1), the superdisintegrant is present therein at a concentration of from 0.1 to 10% by weight, preferably at a concentration of from 0.5 to 5% by weight. In an especially preferred embodiment, the active-substance-comprising bait layer (1) comprises the superdisintegrant at a concentration of from 1 to 2% by weight. Preferably, the superdisintegrants are employed in the form of solid particles with a particle size of less than 65 µm, preferably between 25 and 35 µm.

In a preferred embodiment, the superdisintegrant employed is carboxymethylcellulose. This is in particular the sodium salt of a crosslinked, partially O-carboxymethylated cellulose with the CAS reg. No. 9004-32-4. Synonyms of this substance, which is available under a large number of brand names, are, for example, Croscarmellose, Primellose or "Cellulose, carboxymethyl ether, sodium salt, low-substituted". (US Drug Master File 9662).

In another preferred embodiment, the superdisintegrant employed is carboxymethyl starch. This is in particular the sodium salt of a crosslinked, partially O-carboxymethylated potato or corn starch. The sodium content may be between 2.0 and 5.0%. The substance has the following structure:

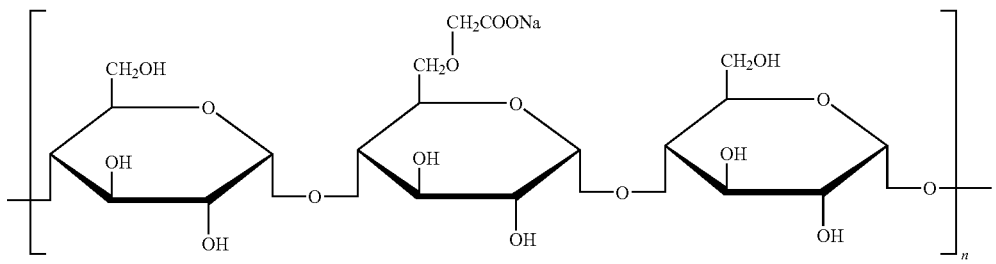

This is a starch derivative with the CAS No. 9063-38-1. The molecular weight of this substance is typically between 500 000 and 11 000 000. The substance is employed in the form of solid particles with a diameter of between 10 and 100 µm. Synonyms of this substance are, for example, Primojel or "Starch, carboxymethyl ether, monosodium salt". (US Drug Master File 3015).

The abovementioned superdisintegrants may also be used generally for reducing the risk of the dissolution of a sugar-comprising layer in an environment with elevated atmospheric humidity, without it being necessary for this layer to comprise an insecticide. Such a sugar-comprising layer (for example the sugar icing of a cake or biscuit) may comprise one of the disclosed sugars in a concentration of up to 99.5% by weight, preferably between 50 and 95% by weight, and a superdisintegrant in a concentration of from 0.1 to 10% by weight, preferably 0.5 to 2% by weight. Such an—insecticide-free—sugar-comprising layer may also have a larger areal weight than the active-substance-comprising bait layer (1), for example 50 to 1500 g/m$^2$.

In a particular embodiment, the active-substance-comprising bait layer (1) can comprise at least one surfactant. Surfactants are known as surface-active agents which bring about the partial or complete wetting of a surface.

Surfactants which are employed are anionic, cationic, nonionic or amphoteric detergents.

Suitable anionic detergents are sulphonated and sulphated alkyl, arylalkyl and alkylaryl compounds, alkylsuccinates, alkylsulphosuccinates and N-alkoylsarcosinates. Preferred are sodium salts, magnesium salts, ammonium salts and the mono-, di- and triethanolamine salts of alkyl and arylalkyl sulphates, and the corresponding salts of alkylarylsulphonates. The alkyl groups of detergents generally have from 12 to 21 carbon atoms and may be unsaturated, but are preferably saturated. It is also possible to employ alkyl ether sulphates which comprise from 1 to 10 ethylene oxide or propylene oxide units per molecule.

Typical suitable anionic detergents which can be employed in accordance with the invention are sodium lauryl sulphate, sodium lauryl ether sulphate, ammonium lauryl sulphate, triethanolamine lauryl sulphate, sodium $(C_{14-16})$-olefinsulphonates, sodium myristyl ether sulphate, ammonium lauryl ether sulphate, disodium lauryl sulphosuccinate, ammonium lauryl sulphosuccinate, sodium dodecylbenzyl sulphonate, sodium cocoyl isethionate and sodium N-lauroylsarcosinate. An especially preferred surfactant in the product according to the invention is sodium cocoamphoacetate.

Suitable cationic detergents are monoquaternary or bisquaternary ammonium compounds which have attached to them at least one long-chain aliphatic radical having 10 to 26 carbon atoms. This long-chain aliphatic radical may comprise an ester bond or an amide bond. Hexadecylmethylammonium chloride is preferred.

Nonionic detergents which can be employed are condensates of ethylene oxide or propylene oxide and a long-chain alcohol, a long-chain amine or a long-chain carboxylic acid, as long as they are not liquid. Here, the aliphatic carbon chain will, as a rule, comprise from 8 to 20 carbon atoms and can be condensed with 5 to 20 ethylene oxide or propylene oxide units. Nonionic detergents which may also be employed are alkyl polyglycosides having 8 to 14 carbon atoms in the alkyl chain.

Amphoteric detergents which are employed are namely betaines which have attached to them long alkyl groups. These include cocodimethylcarboxymethylbetaine, lauryldimethylcarboxymethylbetaine, lauryldimethyl-α-carboxyethylbetaine, cetyldimethylcarboxymethylbetaine, but also sulphobetaines such as cocodimethyl-sulphodimethylbetaine and amido- and amidosulpho-betaines. The carboxybetaines and the amidobetaines are especially preferred. Specific examples are cocoamidopropylbetaine, laurylamidopropylbetaine, myristylamidopropylbetaine and mixtures of the abovementioned compounds.

The at least one surfactant is present in the active-substance-comprising bait layer in an amount of up to 5% by weight, preferably up to 2% by weight. In an especially preferred embodiment, the surfactant is present in the active-substance-comprising bait layer (1) in an amount of between 0.1 and 0.5% by weight.

The protective paper (5) serves to protect the active-substance-comprising bait layer (1) while the product is stored.

The protective paper (6) serves to protect the adhesive layer (3) while the product is stored.

Suitable protective papers may consist of a metal foil, a plastic film, paper or a laminate. The protective papers (5) and (6) preferably have antiadhesive properties imparted to them on the side which faces the layer to be protected, for example by coating with silicone. The protective papers may be printed on the side facing away from the layer to be protected.

The product may also comprise an anchoring layer (4) located between the backing film (2) and the active-substance-comprising bait layer (1) and which brings about better fixing of the constituents of the active-substance-comprising bait layer (1) on the backing film (2).

The thickness of the anchoring layer (4) may be up to 25 μm, with a thickness of from 3 to 10 μm being preferred. The thickness of the anchoring layer (4) may be approximately constant. In a preferred embodiment, however, the thickness of the anchoring layer (4) is not constant, which can be attributed to the presence of regular or irregular recesses ("dimples"). In an especially preferred embodiment, these recesses in the anchoring layer have a regular geometric shape, for example round, oval, diamond-shaped, rectangular or square.

In a preferred embodiment, the anchoring layer (4) has regularly arranged square recesses with an edge length of from 0.5 to 3 mm, preferably from 0.8 to 2 mm and especially preferably 1 mm, so that in total it has the shape of a grid. Here, webs of the grid are from 5 to 25, preferably from 8 to 15 and especially preferably 10 μm in height. If such recesses are present in the anchoring layer (4) they are preferably on that side of this layer which borders the active-substance-comprising bait layer (1).

Suitable materials for the anchoring layer (4) are synthetic polymers. Preferred polymers are those which form the base for water-based coatings, such as, for example, dispersions based on styrene acrylates (for example Luhydran® S 937 T), polyvinyl acetate, phenol resins, PVC, polyvinyl ethers, polyvinyl propionate, PVP homopolymers, PVP copolymers, poly(meth)acrylates, polystyrene, hydrocarbon resins, polyurethane or polyurethane hybrids.

The anchoring layer is preferably congruent with the active-substance-comprising bait layer (1). It is used in particular when the active-substance-comprising bait layer (1) only features incomplete cohesion.

The anchoring layer can be prepared by roller application, painting on, casting, spraying or—preferably—by a printing process. Suitable in this context is in particular rotary screen printing. In the case of an anchoring layer with recesses, the first-mentioned techniques require that suitably shaped stencils are placed on the backing film (2) so that the areas intended to form the recess are not wetted by the polymer used as the material for the anchoring layer. In the case of printing processes, it is possible to use such printing rollers. However, it is also possible to use printing rollers with raised parts so that only those areas of the backing film (2) which are to be printed are wetted by the polymer used as the material for the anchoring layer.

Suitable decorative elements are, for example, motifs of flowers, holograms, objects with shadows which suggest three-dimensionality and specific signal colours.

These motifs, which act as visual stimulus for the target insect, can preferably by printed onto the backing film (2). Colouring the transparent backing film in a signal or attractant colour (yellow, red and the like) may also serve this purpose.

For the purposes of the present description, insects are understood as meaning, in particular, hygiene pests such as ants (Formicidae), horseflies (Tabanidae), flies (Brachycera), mosquitoes (Culicidae), cockroaches (Blattaria), silverfish (Lepismatidae), bugs (Cimicidae) and wasps (Vespinae), some of which may even transmit dieses to humans and animals.

Especially preferred "target insects" are the housefly (*Musca domestica*) and the fruit fly (*Drosophila melanogaster*).

A single product may have a surface area of between 10 and 300 cm², preferably between 50 and 150 cm². A single product may comprise between 2 and 50 mg of an insecticide. That product may be rectangular, in the form of a strip, oval or round, with the round shape being preferred for the form of a window sticker.

The period of usage of a single product may be up to 7 months, it being possible to use the product in an environment with a relative atmospheric humidity of from 40 to 100%, preferably at least 80%, without running ("sagging") of the active-substance-comprising bait layer (1) being observed.

The invention also relates to a process for the preparation of a product comprising an active-substance-comprising bait layer (1) and a backing film (2), where, in a first step, at least one bait substance, at least one insecticide and, if appropriate, at least one substance from the group of the adjuvants which act as solvent for the insecticide and/or the bait substance, of the auxiliaries, of the attractants, of the surfactants and of the bittering agents are mixed, in a second step, a superdisintegrant is added to this mixture and the mixture thus obtained subsequently applied to the backing film (2), where, if appropriate, an anchoring layer (4) is applied to this side of the backing film before the mixture obtained in step two is applied to the backing film (2).

The invention also relates to the use of a superdisintegrant from the group consisting of carboxymethylcellulose and/or carboxymethyl starch for reducing the risk of dissolution of a sugar-comprising layer in an environment with elevated atmospheric humidity, where the layer comprises at least 50% by weight of a sugar and preferably has an areal weight of from 50 to 1500 $g/m^2$.

Finally, the invention also relates to a method of attracting and destroying insects, in particular ants (Formicidae), horseflies (Tabanidae), flies (Brachycera), mosquitoes (Culicidae), cockroaches (Blattaria), silverfish (Lepismatidae), bugs (Cimicidae) and wasps (Vespinae), where a product which comprises an active-substance-comprising bait layer (1) and a backing film (2) is exposed to these insects in such a manner that the insects are capable of taking up the active substance—preferably an insecticide—simultaneously with the bait substance.

The examples which follow are intended to illustrate the preparation of the product.

EXAMPLE 1

844.49 g of glucose syrup are weighed into a container capable of being heated. An active substance solution of 36.5 g of acetamiprid and 73 g of N-octylpyrrolidone is added to the glucose syrup, with stirring, and the mixture is stirred for approximately 30 minutes at 40° C. Thereafter, 1.7 g of a 5% strength aqueous Bitrex solution, 2.5 g of sodium lauryl sulphate and 41.5 g of Primellose are added in succession, and the mixture is stirred until a milky homogeneous suspension has formed.

Using a screen-printing machine, this composition is subsequently printed in the print motif area onto a 50 μm polyethylene terephthalate backing film (2) which is equipped with pressure-sensitive adhesive and printed with flowers. After the water has been removed by drying at an elevated temperature, the active-substance-comprising bait layer (1) which has now formed has an areal weight of 20 $g/m^2$.

This laminate is punched in such a way that round punchings with a sunflower motif and a diameter of approximately 10 cm are formed. A silicone-treated paper which acts as the protective layer (5) is placed onto the resulting laminate, and the entire laminate is cut into a card 100×220 mm in size. This individual card with two products in the form of sunflower stickers is packaged in side-sealed bags.

EXAMPLE 2

888.5 g of glucose syrup are weighed into a container capable of being heated. 66.3 g of etofenprox, 1.6 g of a 5% strength aqueous Bitrex solution, 2.5 g of Dehyton and 41.0 g of Primojel are added, with stirring, to the glucose syrup and the mixture is stirred at 40° C. The mixture is stirred until an oily suspension with a homogeneous appearance has formed.

This composition is subsequently spread onto a 100 μm polypropylene backing film (2) provided with a pressure-sensitive adhesive. After the water has been removed by drying at an elevated temperature, the active-substance-comprising bait layer (1) which has now formed has an areal weight of 50 $g/m^2$.

This laminate is punched into strips so that 6 strips 10 mm×200 mm in size are formed on an area of 60×200 mm. A silicone-treated paper which acts as the protective layer (5) is placed onto the resulting striped laminate and cut into a card 60 mm×200 mm in size. Two of these individual cards with in each case 6 strips are packaged in a folded box.

EXAMPLE 3

844.49 g of glucose syrup are weighed into a container capable of being heated. An active substance solution of 36.5 g of acetamiprid and 73 g of N-octylpyrrolidone is added to the glucose syrup, with stirring, and the mixture is stirred for approximately 30 minutes at 40° C. Thereafter, 1.7 g of a 5% strength aqueous Bitrex solution, 2.5 g of Dehyton and 41.5 g of Primellose are added in succession, and the mixture is stirred (for approx. 30 minutes) until a suspension with a homogeneous appearance has formed.

Using a coating box, this composition is applied at a thickness of approximately 120 μm to a PET/board/PET laminate which had previously been provided on the back side with a double-sided adhesive tape with protective cover. After the water has been removed by drying at an elevated temperature, the active-substance-comprising bait layer (1) which has now formed has an areal weight of 100 $g/m^2$. The board/bait laminate is covered with a paper which had been treated on one side with silicone and is subsequently provided in three places with crossfolds so that fold lines which are clearly visible to the user are formed. After 200 mm, the laminate is cut transversely, and the resulting triangular baits (for example 65 mm×200 mm) are packaged in tubular bags.

The present invention relates to a product for attracting and destroying insects (in particular flies), preferably in the form of a sticker to be stuck onto windowpanes. The invention furthermore relates to the preparation of this product and to its use on domestic premises, in kitchens, in gastronomy, in agriculture and in industry.

Products for attracting and destroying insects are known. These products which are known as "attract-and-kill" products also include fly window stickers of the Blattanex® brand from Bayer CropScience Deutschland GmbH.

These fly window stickers are bait stickers for sticking onto windowpanes in places which houseflies like to visit. The flies are attracted by the shape and the combination of feed substance and/or bait attractant, are encouraged to eat, and die. A single product should have a duration of action of one fly season, i.e. approximately 4 to 7 months.

The disadvantage of these known fly window stickers is that both water (water of condensation or water used for wiping) and high atmospheric humidity can adversely affect the activity. They must therefore be protected from water and moisture. Experiments have shown that, when used in rooms with elevated atmospheric humidity (the kitchen of private domestic premises or gastronomic operations, bathroom), the layer which contains the combination of feed substance and/or bait attractant and an insecticidal active substance tends to dissolve. This phenomenon also has an adverse effect on the performance of the product due to a shorter duration of action.

It is now possible for the end user to fold the laminate at the crossfolds before using the product. To this end, the user must first remove the protective film from the "fixing adhesive" (3).

The triangle formed by folding is glued together by means of the fixing tape and now forms a trap capable of being erected.

LIST OF REFERENCE SYMBOLS

Figure 1:
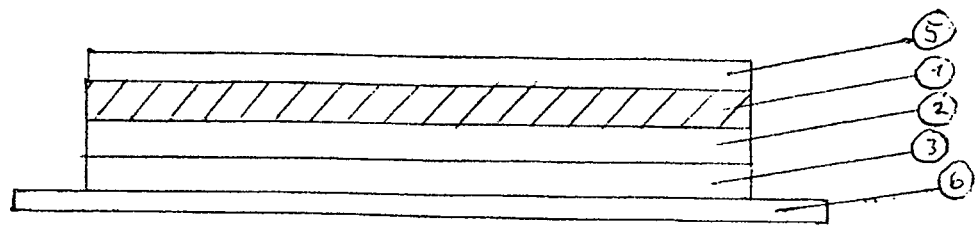
FIG. 1 shows a cross-section of the schematic construction of a product.
Figure 2:
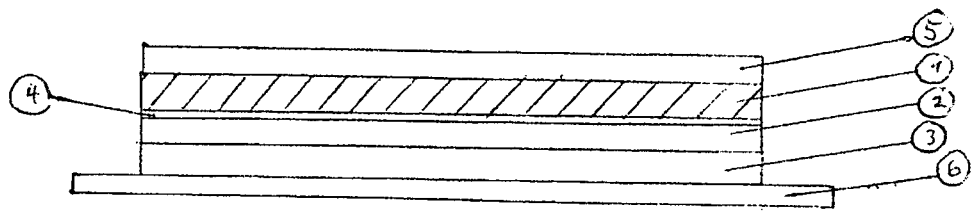
FIG. 2 shows a cross-section of the schematic construction of a product, with an anchoring layer (4) additionally being present between the active-substance-comprising bait layer (1) and the backing film (2).
Figure 3:
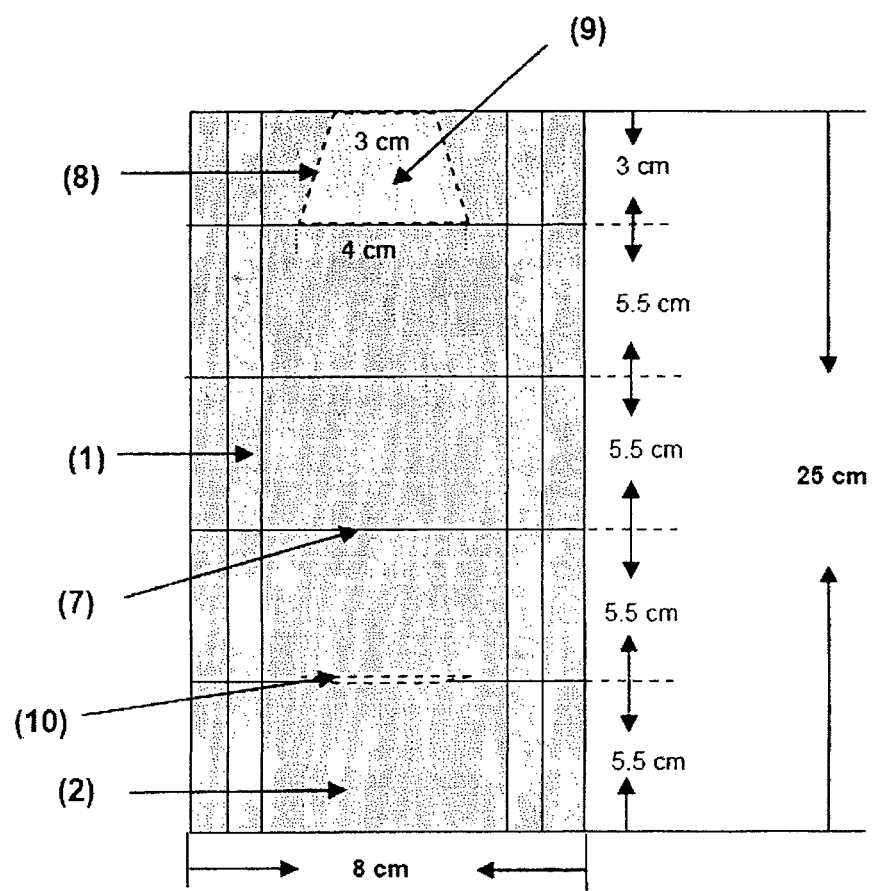
FIG. 3 shows the product in the form of a backing film which features the active-substance-comprising bait layer (1) in the form of two longitudinal strips and which is provided with cutting lines (8) and fold lines (7). Folding along the fold lines (7) makes it possible to insert the tab (9) into the cutting line (10) and so to make, from the backing film (2), a trap capable of being erected.

In the figures, the numbers have the following meanings:
1=active-substance-comprising bait layer
2=backing film
3=adhesive layer
4=anchoring layer
5=protective paper
6=protective paper
7=fold line
8=cutting lines

We claim:

1. A product for attracting and destroying insects, comprising:
    an active-substance-comprising bait layer; and
    a backing film;
    wherein the active-substance-comprising bait layer comprises:
        at least 30% by weight of a bait substance;
        at least 0.1% to no more than 25% by weight of at least one insecticide; and
        at least 0.1% to no more than 10% by weight of at least one superdisintegrant selected from the group consisting of carboxymethylcellulose, carboxymethyl starch, and crosslinked polyvinylpyrrolidone; and
    wherein the superdisintegrant is in the form of solid particles with a particle size of less than 65 μm.

2. The product according to claim 1;
wherein the bait substance includes at least one sugar.

3. The product according to claim 1;
wherein the concentration of the bait substance in the active-substance-comprising bait layer is up to 99.5% by weight.

4. The product according to claim 1;
wherein the at least one insecticide is selected from the group consisting of pyrethrum, organophosphorous insecticides, carbamates, pyrethroids, phenylpyrazoles, neonicotinoids, and biopesticides.

5. The product according to claim 1;
wherein the at least one insecticide is selected from the group consisting of abamectin, acetamiprid, alpha-cypermethrin, azadirachtin (neon), azamethiphos, beta-cyfluthrin, bifenazate, bifenthrin, buprofezin, chlorantraniliprole, chlorfenapyr, chlorpyrifos, clothianidin, deltamethrin, diflubenzuron, dinotefuran, dimethoate, esfenvalerate, etofenprox, fenoxycarb, fenpyroximate, flonicamid, flubendiamid, flufenoxuron, imidacloprid, imiprothrin, indoxacarb, potash soap, kieselguhr, lambda-cyhalothrin, lithium perfluoroctanesulphonate, magnesium phosphide, metaflumizone, methoxyfenozide, metofluthrin, milbemectin, mineral oils, n-methylneodecanamide, nicarbazin, novaluron, pirimicarb, pirimiphos-methyl, pymetrozine, pyrethrins, pyridalyl, rapeseed oil, spinosad, spirodiclofen, sulphuryl fluoride, tebufenozide, tefluthrin, thiacloprid, thiamethoxam, zeta-cypermethrin, Bacillus thuringiensis subspecies, Mexican Cydia pomonella granulovirus, and combinations of abamectin and thiamethoxam, azamethiphos and fipronil, beta-cyfluthrin and clothianidin, beta-cyfluthrin and imidacloprid, cyfluthrin and codlemone, fludioxonil and metalaxyl-M and thiamethoxam, fuberidazole and imazalil and triadimenol and imidacloprid, methiocarb and imidacloprid, pencycuron and imidacloprid, pyrethrins and abamectin, pyrethrins and rapeseed oil, and tefluthrin and imidacloprid.

6. The product according to claim 1;
wherein the at least one insecticide used is acetamiprid, azamethiphos, ethofenprox, fipronil, imidacloprid, at least one pyrethroid, thiacloprid, or the combination of azamethiphos and fipronil.

7. The product according to claim 1;
wherein the superdisintegrant in the active-substance-comprising bait layer is present in a concentration of between 0.5 and 5% by weight.

8. The product according to claim 1;
wherein the active-substance-comprising bait layer comprises at least one surfactant from the group consisting of anionic, cationic, nonionic, and amphoteric detergents.

9. The product according to claim 1;
wherein the active-substance-comprising bait layer has an areal weight of between 10 and 250 g/m$^2$.

10. The product according to claim 1;
wherein the concentration of a surfactant in the active-substance-comprising bait layer amounts to no more than 5% by weight.

11. The product according to claim 1, further comprising:
an anchoring layer between the active-substance-comprising bait layer and the backing layer.

12. The product according to claim 11;
wherein the anchoring layer has a thickness of up to 25 μm.

13. The product according to claim 1;
wherein the active-substance-comprising bait layer is present in the form of at least one of dots, strips, and a rigid foam.

14. The product according to claim 1;
wherein the active-substance-comprising bait layer comprises at least one adjuvant selected from a group consisting of
    solvents for at least one of the insecticide and the bait substance, attractants, tittering agents, binders, UV absorbers, pH buffers, salts, antiageing agents, fillers, plasticizers, odour-masking agents, deoxidizers, antistatics, stabilizers, separating agents, glidants, flame retardants, microbicides, viscosity enhancers, dispersants, optical brighteners, colorants, and flavorings.

15. The product according to claim 1;
wherein the superdisintegrant is carboxymethylcellulose.

16. The product according to claim 1;
wherein the superdisintegrant is crosslinked polyvinylpyrrolidone.

17. The product according to claim 1;
  wherein the concentration of the bait substance in the active-substance-comprising bait layer is between 50 and 95% by weight.
18. The product according to claim 1;
  wherein the concentration of the bait substance in the active-substance-comprising bait layer is between 70 and 90% by weight.
19. The product according to claim 1;
  wherein the superdisintegrant in the active-substance-comprising bait layer is present in a concentration of between 1 and 2% by weight.
20. The product according to claim 1;
  wherein the active-substance-comprising bait layer comprises at least one surfactant from the group consisting of:
    anionic detergents selected from the group consisting of sulphonated and sulphated alkyl, arylalkyl and alkylaryl compounds, alkylsuccinates, alkylsulphosuccinates, and N-alkoylsarcosinates;
    cationic detergents selected from the group consisting of monoquaternary and bisquaternary ammonium compounds which have attached to them at least one aliphatic radical which has 10 to 26 carbon atoms and which may comprise an ester bond or an amide bond;
    nonionic detergents selected from the group consisting of condensates of ethylene oxide or propylene oxide and a long-chain alcohol, a long-chain amine or a long-chain carboxylic acid, where the hydrocarbon chain comprises 8 to 20 carbon atoms and is condensed with 5 to 20 ethylene oxide or propylene oxide units, and alkylpolyglycosides having 8 to 14 carbon atoms in the alkyl chain; and
    amphoteric detergents which are betaines.
21. The product according to claim 1;
  wherein the active-substance-comprising bait layer comprises at least one adjuvant selected from a group consisting of:
    solvents for at least one of the insecticide and the bait substance, selected from the group consisting of aliphatic hydrocarbons, aromatic hydrocarbons, hydroaromatic hydrocarbons, terpene hydrocarbons, alcohols, esters, ethers, glycol ethers, ketones, chlorohydrocarbons, aldehydes, acetals, aliphatic saturated monocarboxylic acids, natural, and synthetic polymers;
    attractants selected from the group consisting of sexual pheromones and aggregation pheromones which are produced by the insects themselves; and
    bittering agents, binders, UV absorbers, pH buffers, salts, antiageing agents, fillers, plasticizers, odour-masking agents, deoxidizers, antistatics, stabilizers, separating agents, glidants, flame retardants, microbicides, viscosity enhancers, dispersants, optical brighteners, colorants, and flavorings.
22. The product according to claim 1;
  wherein the active-substance-comprising bait layer comprises at least one adjuvant selected from a group consisting of:
    1-octanol, 1-decanol, acetone, acetophenone, benzyl alcohol, butyrolactone, hexyl laurate, PEG-60 corn glycerides, citrus terpenes, dimethylformamide, dimethyl sulphoxide, acetic acid, ethanol, ethyl acetate, ethylene glycol, eucalyptol, glycerol, isopropyl myristate, methyl ethyl ketone, morpholine, lavender/citronella mixtures, myrcene, neodecanoic acid, N-methyl-2-pyrrolidone, N-octylpyrrolidone, oleic acid, PEG 400, and tributyl phosphate.

\* \* \* \* \*